United States Patent [19]

Kurmeier et al.

[11] Patent Number: 4,987,133
[45] Date of Patent: Jan. 22, 1991

[54] SALICYLIC ACID DERIVATIVES

[75] Inventors: Hans-Adolf Kurmeier, Seeheim-Jugenheim; Wolf-Dietrich Weber, Reinheim; Hans-Eckart Radunz, Mühltal; Hans-Jochen Schliep, Traisa, all of Fed. Rep. of Germany

[73] Assignee: Merck Patent Gesellschaft Mit Beschrankter Haftung, Darmstadt, Fed. Rep. of Germany

[21] Appl. No.: 338,822

[22] Filed: Apr. 17, 1989

[30] Foreign Application Priority Data

Apr. 16, 1988 [DE] Fed. Rep. of Germany ....... 3812755

[51] Int. Cl.⁵ .................. A61K 31/495; A61K 31/55; C07D 417/04; C07D 405/04
[52] U.S. Cl. .................................... 514/252; 514/218; 514/307; 514/329; 514/399; 514/415; 540/575; 544/369; 544/374; 546/146; 546/147; 546/224; 548/337; 548/341; 548/506
[58] Field of Search ................ 540/575; 544/369, 374; 514/218, 252

[56] References Cited

U.S. PATENT DOCUMENTS 3,489,757  1/1970  Koppe et al. ................ 544/377
4,255,575  3/1981  Grisar et al. ................ 544/394

OTHER PUBLICATIONS

Grisar et al., *J. Med. Chem.* pp. 327–336 (1981).
Archibald et al., Chemical Abstracts, vol. 77, No. 34355 (1972).
Archibald et al., Chemical Abstracts, vol. 79, No. 136989 (1973).

*Primary Examiner*—Mukund J. Shah
*Assistant Examiner*—E. Bernhardt
*Attorney, Agent, or Firm*—Millen, White & Zelano

[57] ABSTRACT

New salicylic acid derivatives of the general formula I

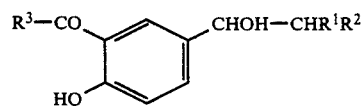

in which
$R^1$ is H or $CH_3$,
$R^2$ is 4-(4-methyl-2-thiazolyl)-piperazino, 4-(tetrahydro-2-furoyl)-piperazino, 4-(4-methyl-2-thiazolyl)-homopiperazino, 4-benzamidopiperidino, 6,7-dimethoxy-1,2,3,4-tetrahydroisoquinolino, 1-imidazolyl, tribromo-1-imidazolyl or 2-(3-indolyl-1,1-dimethyl-ethylamino and
$R^3$ is alkoxy having 1-4 C atoms, $NH_2$ or alkylamino having 1-4 C atoms, as well as the physiologically acceptable acid addition salts thereof, exhibit effects on the circulation, especially effects lowering the blood pressure and relieving the heart, and diuretic effects.

14 Claims, No Drawings

SALICYLIC ACID DERIVATIVES

SUMMARY OF THE INVENTION

The invention relates to new salicylic acid derivatives of the general formula I

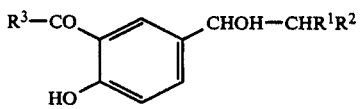

in which $R^1$ is H or $CH_3$, $R^2$ is 4-(4-methyl-2-thiazolyl)-piperazino, 4-(tetrahydro-2furoyl)-piperazino, 4-(4-methyl-2-thiazolyl)-homopiperazino, 4-benzamidopiperidino, 6,7-dimethoxy-1,2,3,4-tetrahydroisoquinolino 1-imidazolyl, tribromo-1-imidazolyl or 2-(3-indolyl)-1,1-dimethyl-ethylamino and $R^3$ is alkoxy having 1-4 C atoms, $NH_2$ or alkylamino having 1-4 C atoms, as well as the physiologically acceptable acid addition salts thereof.

Similar compounds are described in DE-OS 2,144,080 and DE-OS 2,302,717.

The invention further relates to finding new compounds which can be used to prepare pharmaceuticals. This has been achieved by providing the compounds of the formula I.

It has been found that the compounds of the formula I and the physiologically acceptable acid addition salts thereof have valuable pharmacological properties associated with satisfactory tolerability. Thus, for example, effects on the circulation, especially effects lowering the blood pressure and relieving the heart, and consequently cardioprotective effects, are found.

The substances reduce, for example, the blood pressure measured in the carotid loop of the conscious mongrel dog (for method, see E. C. van LEERSUM, Pflugers Archiv 142, 377–395 (1911)) in animals with nephrogenic hypertension (for method, see I. H. PAGE, Science 89, 273–274 (1939)) in the experiment lasting 10 days on oral administration of doses which may be lower than 2 mg/kg/day, dose-dependently to a lower level.

Furthermore, the arterial blood pressure measured directly in conscious spontaneously hypertensive rats (strain SHR/NIH-MO/CHB-EMD) carrying catheters, (for method, see J. R. WEEKS and J. A. JONES, Proc. Soc. Exptl. Biol. Med. 104, 646–648 (1960)) is lowered dose-dependently after a single intragastric dose of 10 mg/kg or above.

The effect relieving the heart can be deduced from the following cardiovascular effects, observed after intravenous administration to the anaesthetized dog:

(1) increase in the total vascular capacity (method: H. SUGAR et al., Pflügers Archiv, 361, 95–98 (1975));

(2) afterload reduction and decrease in cardiac performance (method: K. STEPHAN et al., Arzneimittelforschung, 25, 1770–1776 (1975)).

The increase in the tolerance of ischemia of the heart by the substances according to the invention can be demonstrated on the anaesthetized dog using the method of reversible coronary artery occlusion (P. R. MAROKO et al., Circulation 43, 67–82 (1971)) and on the anaesthetized pig with restricted coronary blood supply (method: P. D. VERDOUW et al., European Heart Journal, 4 (suppl. C), 61–67 (1983)).

The compounds of the formula I and the physiologically acceptable acid addition salts can therefore be used as medicinal active substances in human and veterinary medicine and as intermediates for the preparation of other medicinal active substances. In particular, the esters of the formula I ($R^3$=alkoxy having 1-4 C atoms) also serve as intermediates for the preparation of the amides of the formula I.

One aspect of the invention is to provide compounds of the formula I and physiologically acceptable acid addition salts thereof. Another aspect of this invention is to provide pharmaceutical compositions comprising these compounds. A third aspect of the invention is the treatment of diseases of the cardiovascular system, for example high blood pressure, with compounds of this invention.

Upon further study of the specification and appended claims, further objects and advantages of this invention will become apparent to those skilled in the art.

The radical $R^1$ in the formula I is preferably H. The radical $R^2$ is preferably 4-(4-methyl-2-thiazolyl)-piperazin. $R^3$ is preferably an $NH_2$ group.

Accordingly, the invention particularly relates to those compounds of the formula I in which at least one of the said radicals has one of the meanings indicated above as preferred.

A preferred group of compounds corresponds to the formula I in which $R^1$ and $R^3$ have the stated meanings and $R^2$ is 4-(4-methyl-2-thiazolyl)-piperazino, 4-(tetrahydro-2-furoyl)-piperazino, 4-(4-methyl-2-thiazolyl)-homopiperazino, 6,7-dimethoxy-1,2,3,4-tetrahydroisoquinolino, 1-imidazolyl, tribromo-1-imidazolyl or 2-(3-indolyl)-1,1-dimethyl-ethylamino.

The invention furthermore relates to a process for the preparation of the compounds of the formula I, as well as of the physiologically acceptable acid addition salts thereof, characterized in that a salicylic acid derivative of the general formula II

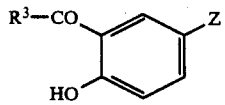

in which
Z is —CHOH—CHR$^1$—X or

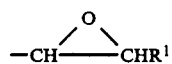

and X is Cl, Br, I or a reactive functionally modified hydroxyl group, and $R^1$ and $R^3$ have the stated meanings, is reacted with a base of the general formula III

H-R$^2$                                                                III in which
$R^2$ has the stated meaning,
or in that a compound which otherwise corresponds to formula I but in place of one or more H atoms contains one or more reducible groups and/or C—C bonds and/or C—N bonds is reduced and/or in that, where appropriate, an ester of the formula I ($R^3$=alkoxy having 1-4 C atoms) is converted by reaction with a compound of the formula $R^4$-$NH_2$ in which $R^4$ is H or alkyl having 1–4 C atoms into an amide of the formula I ($R^3$=$NH_2$ or alkylamino having 1–4 C atoms) and/or a base of the formula I is converted by treatment with an acid into one of the physiologically acceptable acid addition salts thereof.

X in the compounds of the formula II is preferably Cl, Br, I or arylsulfonyloxy having 6–10 C atoms such as benzene- or p-toluenesulfonyloxy.

The compounds of the formula I can be prepared by methods known per se and as are described in the literature (for example in the standard works such as HoubenWeyl, Methoden der Organischen Chemie, (Methods of organic chemistry), published by Georg-Thieme, Stuttgart), specifically under reaction conditions as are known per se and suitable for the conversions described hereinafter. In this connection, it is also possible to make use of variants which are known per se but not mentioned here in detail.

The starting materials can, if desired, also be prepared in situ in such a manner that they are not isolated from the reaction mixture but are immediately reacted further to give the compounds of the formula I.

One preparation of the salicylic acid derivatives of the formula I from the compounds of the formulae II and III is preferably carried out in the presence of an inert solvent, for example of an alcohol such as methanol, ethanol or isopropanol or of an ether such as diethyl ether, tetrahydrofuran or dioxane, at temperatures between about 0° and 120°, preferably between 20° and 100°. It may be advantageous to add a base such as triethylamine or pyridine. It is also possible to work without a solvent or to use an excess of the base III as solvent.

The starting materials of the formulae II and III are mostly known. Those which are unknown can easily be prepared in analogy to methods known per se. For example, salicylic acid derivatives of the formula o-$R^3$—CO—$C_6H_4$—OH can be acylated with chloroacetyl chloride or bromoacetyl bromide/$AlCl_3$ to give the corresponding 5-haloacetyl salicylic acid derivatives, and the latter can be reduced to the 5-haloethanols of the formula II (Z=—CHOH—$CH_2Cl$ or —CHOH—$CH_2Br$). Correspondingly, the 5-halopropionyl-salicylic acid derivatives and the corresponding 5-halopropanols can be obtained using halopropionyl halides. The epoxides of the formula II

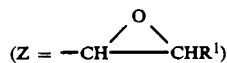

can be obtained from the halo-alcohols by dehydrohalogenation.

Preferred starting materials for the preparation of the compounds of the formula I by reduction correspond to the formula IV

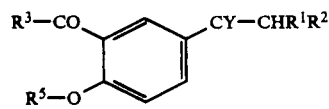

in which
Y is =O or (H, OH) and $R^5$ is H or a group which can be eliminated by hydrogenolysis, preferably benzyl, but in which Y is not (H, OH) at the same time as $R^5$ is H.

The reduction can be carried out, for example, by catalytic hydrogenation at temperatures between about 0° and about 200° C. and under pressures between about 1 and 200 bar in an inert solvent, for example one of the said alcohols or ethers, an ester such as ethyl acetate, or a carboxylic acid such as acetic acid. Suitable and preferred catalysts are noble metals such as Pt or Pd which can be used in the form of oxides (for example $PtO_2$, PdO), on a support (for example Pd on charcoal, calcium carbonate or strontium carbonate) or in finely divided form. Keto groups can also be reduced using complex metal hydrides, it of course being necessary for the other functional groups in the molecule not to be attached. A particularly suitable reducing agent is $NaBH_4$, which can be used in one of the said alcohols, if desired with the addition of other solvents such as water and/or tetrahydrofuran, at temperatures between about −10° and +50°. Examples of other suitable reducing agents are $LiBH_4$, $Zn(BH_4)_2$, $LiAlH_4$ and triisobutylaluminium hydride in ethers such as tetrahydrofuran or dioxane. It is particularly advantageous to prepare salicylic esters of the formula I ($R^3$=alkoxy having 1–4 C atoms) in this manner.

The starting materials of the formula IV (Y==O) can be obtained, for example, by reaction of salicylic acid derivatives of the formula o-$R^3$—CO—$C_6H_4$—OH with bromoacetyl bromide to give the corresponding 5-bromoacetal-salicylic acid derivatives and reaction with III.

An ester of the formula I ($R^3$=alkoxy having 1–4 C atoms) can be converted with a base of the formula $R^4NH_2$ into the corresponding amide of the formula I ($R^3$=$NH_2$ or alkyl having 1–4 C atoms), preferably in the presence of an inert solvent, for example one of the alcohols indicated, at temperatures between about −20° and +80°.

A base of the formula I can be converted with an acid into the relevant acid addition salt. Suitable for this reaction are acids which provide physiologically acceptable salts. Thus, it is possible to use inorganic acids, for example sulfuric acid, hydrohalic acids such as hydrochloric acid or hydrobromic acid, phosphoric acids such as orthophosphoric acid, nitric acid, sulfamic acid, as well as organic acids, specifically aliphatic, alicyclic, araliphalic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric malicacid benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono-and -disulfonic acids, and lauryl sulfuric acid.

The free bases of the formula I can, if desired, be liberated from their salts by treatment with strong bases such as sodium or potassium hydroxide or sodium or potassium carbonate.

The compounds of the formula I may possess one or more centers of asymmetry. They may therefore result from their preparation as racemates or else, if optically active starting materials are used, in optically active form. If the compounds have two or more centers of asymmetry, then the synthesis generally results in mixtures of racemates, from which the individual racemates can be isolated in pure form, for example by recrystallization from inert solvents. Racemates which have been obtained can, if desired, be resolved into their optical antipodes mechanically or chemically by methods known per se. Preferably, diastereomers are formed from the racemate by reaction with an optically active resolving agent. Examples of suitable resolving agents are optically active acids such as the D and L forms of tartaric acid, dibenzoyltartaric acid, diacetyltartaric acid, camphorsulfonic acids, mandelic acid, malic acid or lactic acid. The various forms of the diastereomers can be separated in a manner known per se, for example by fractional crystallization, and the optically active compounds of the formula I can be liberated from the diastereomers in a manner known per se.

The invention furthermore relates to the use of the compounds of the formula I, and of the physiologically acceptable salts thereof, for the preparation of pharmaceutical compositions, especially by non-chemical means. In this connection, they can be converted into a suitable dosage form together with at least one vehicle or auxiliary and, where appropriate, in combination with one or more other active substance(s).

The invention furthermore relates to agents, especially pharmaceutical compositions, containing at least one compound of the formula I and/or one of the physiologically acceptable acid addition salts thereof.

These compositions can be used as medicaments in human in or veterinary medicine. Suitable vehicles are organic or inorganic substances which are suitable for enteral (for example oral), parenteral or topical administration and do not react with the new compounds, for example water, vegetable oils, benzyl alcohols, polyethylene glycols, gelatin, carbohydrates such as lactose or starch, magnesium stearate, talc, vaseline. Used for enteral administration are, in particular, tablets, coated tablets, capsules, syrups, elixirs, drops or suppositories, for parenteral administration are solutions, preferably oily or aqueous solutions, as well as suspensions, emulsions or implants, and for topical administration are ointments, creams or powders.

The new compounds can also be lyophilized, and the resulting lyophilizates used, for example, for the preparation of products for injection. The stated compositions can be sterilized and/or contain auxiliaries such as lubricants, preservatives, stabilizers and/or wetting agents, emulsifiers, salts to influence the osmotic pressure, buffer substances, colorants, flavorings and/or perfumes. They may also, if desired, contain one or more other active substances, for example one or more vitamins.

The invention furthermore relates to the use of the compounds of the formula I, and of the physiologically acceptable acid addition salts thereof, for the therapeutic treatment of the human or animal body and for controlling diseases, especially all types of hypertension and coronary heart diseases, as well as cardiac, nephrogenic or hepatogenic edemas, and for achieving diuresis.

This entails the substances according to the invention being administered, as a rule, in analogy to known, commercially available products with similar indications (for example molsidomine, dihydralazine, trichlormethiazide or hydrochlorothiazide), preferably in dosages between about 1 and 100 mg, in particular between 5 and 50 mg, per dosage unit. The daily dosage is preferably between about 0.02 and 5 mg/kg of body weight. A specific dose for each particular patient depends, however, on a wide variety of factors, for example on the efficacy of the specific compound used, on the age, body weight, general state of health, and sex, on the diet, on the time and route of administration, on the rate of excretion, medicament combination and severity of the particular disease to which the therapy applies. Oral administration is preferred.

Each of the compounds of the formula I mentioned in the following examples is particularly suitable for the preparation of pharmaceutical compositions.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application German P 38 12 755.5, filed Apr. 16, 1988, are hereby incorporated by reference.

In the examples which follow, "usual working-up" means: if necessary, water, sodium bicarbonate or sodium carbonate solution or dilute sodium hydroxide solution is added, the mixture is extracted with an organic solvent such as chloroform, the phases are separated, the organic extract is evaporated, and purification is by chromatography and/or crystallization of the base or one of its salts. Temperatures are stated in degrees Celsius.

EXAMPLE 1

18.9 g of 1-(4-methyl-2-thiazolyl)-piperazine and 26 g of 5-(2-bromo-1-hydroxyethyl)-salicylamide (obtainable by acylation of salicyamide with bromoacetyl bromide-/AlCl$_3$ to give 5-bromoacetyl-salicylamide and subsequent reaction with NaBH$_4$) are dissolved in 400 ml of ether, 15 ml of triethylamine are added, the mixture is boiled for 2 h and subjected to the usual working-up, and 5-[1-hydroxy-2-(4-(4-methyl-2-thiazolyl)-piperazino)-ethyl]salicylamide ("A"), m.p. 182°, is obtained. Dihydrochloride m.p. 244°–245°.

EXAMPLES 2 to 9

The following are obtained in analogy to Example 1 using 1-tetrahydrofuroylpiperazine, 4-(4-methyl-2-thiazolyl)homopiperazine, 4-benzamidopiperidine, 6,7-dimethoxy-1,2, 3,4-tetrahydroisoquinoline, imidazole, tribromoimidazole, 2-(3-indolyl)-1,1-dimethyl-ethylamine and from 5-(3-bromo-1-hydroxypropyl)-salicylamide with 1(4-methyl-2-thiazolyl)-piperazine:

2. 5-[1-hydroxy-2-(4-tetrahydrofuroyl-piperazino)-ethyl]-salicylamide.

3. 5-[1-hydroxy-2-(4-(4-methyl-2-thiazolyl)-homopiperazino)ethyl]-salicylamide, m.p. 195°.

4. 5-[1-hydroxy-2-(4-benzamidopiperidino)-ethyl]-salicylamide, m.p. 202°5. 5-[1-hydroxy-2-(6,7-dimethoxy-1,2,3,4-tetrahydroisoquinolino)-ethyl]-salicylamide, m.p. 187°.

6. 5-[1-hydroxy-2-(1-imidazolyl)-ethyl]-salicylamide.

7. 5-[1-hydroxy-2-(tribromo-1-imidazolyl)-ethyl]-salicylamide, m.p. 216°.

8. 5-[1-hydroxy-2-(2-(3-indolyl)-1,1-dimethyl-ethylamino)ethyl]-salicylamide, hydrochloride, m.p. 248°.

9. 5-[1-hydroxy-2-(4-(4-methyl-2-thiazolyl)-piperazino)propyl]-salicylamide, dihydrochloride-monohydrate, m.p. 186°

EXAMPLE 10

A solution of 18.9 g of 4-(4-methyl-2-thiazolyl)piperazine and 17.9 g of 5-epoxyethyl-salicylamide [obtainable by dehydrobromination of 5-(2-bromo-1-hydroxyethyl)-salicylamide]in 300 ml of tetrahydrofuran is left to stand overnight. The usual working-up results in "A", m.p. 182°.

The compounds indicated in Examples 2 to 9 are obtainable analogously.

EXAMPLE 11

NaBH$_4$ is added in portions until reaction is complete (checked by TLC) to a solution of 37.5 g of methyl 5-[4-(4-methyl-2-thiazolyl)piperazino-acetyl]-salicylate [m.p. 120°, obtainable by boiling 4-(4-methyl-2-thiazolyl)piperazine with methyl 5-bromacetyl-salicylate in ether in the presence of triethylamine for 2 h]in 100 ml of ethanol, 50 ml of water and 300 ml of tetrahydrofuran under argon at −5° to 0°. The mixture is stirred at 20° for 30 min., acidified with acetic acid and concentrated, and the usual working-up results in methyl 5-[1-hydroxy-2-(4-(4-methyl-2-thiazolyl)-piperazino)-ethyl]-salicylate, m.p. 121°. Dihydrochloride, m.p. 186°.

EXAMPLES 12 to 19

In analogy to Example 11 there are obtained from
methyl 5-(4-tetrahydrofuroyl-piperazino-acetyl)-salicylate
methyl 5-[4-(4-methyl-2-thiazolyl)-homopiperazino-acetyl]salicylate
methyl 5-(4-benzamidopiperidino-acetyl)-salicylate (m.p. 158°)
methyl 5-(6,7-dimethoxy-1,2,3,4-tetrahydroisoquinolinoacetyl)salicylate
methyl 5-(1-imidazolyl-acetyl)-salicylate (m.p. 142°)
methyl 5-(tribromo-1-imidazolyl-acetyl)-salicylate (m.p. 174°)
methyl 5-[2-(3-indolyl)-1,1-dimethyl-ethylamino-acetyl]salicylate methyl-5-[2-(4-(4-methyl-2-thiazolyl)-piperazino)-propionyl]salicylate (dihydrochloride m.p. 191°) with NaBH$_4$ 12. methyl 5-[1-hydroxy-2-(4-tetrahydrofuroyl-piperazino)-ethyl]-salicylate, hydrochloride m.p. 218°.

13. methyl 5-[1-hydroxy-2-(4-(4-methyl-2-thiazolyl)-homopiperazino)-ethyl]-salicylate, dihydrochloride monohydrate m.p. 154°.

14. methyl 5-[1-hydroxy-2-(4-benzamidopiperidino)-ethyl]-salicylate, hydrochloride m.p. 246°.

15. methyl 5-[1-hydroxy-2-(6,7-dimethoxy-1,2,3,4-tetrahydroisoquinolino)-ethyl]-salicylate.

16. methyl 5-[1-hydroxy-2-(1-imidazolyl)-ethyl]-salicylate.

17. methyl 5-[1-hydroxy-2-(tribromo-1-imidazolyl)-ethyl]-salicylate, m.p. 175°.

18. methyl 5-[1-hydroxy-2-(2-(3-indolyl)-1,1-dimethyl)ethylamino)-ethyl]-salicylate, hydrochloride m.p. 201°.

19. methyl 5-[1-hydroxy-2-(4-(4-methyl-2-thiazolyl)-piperazino)-propyl]-salicylate, dihydrochloride m.p. 186°.

EXAMPLES 20 to 25

The following are obtained in analogy to Example 11 from the corresponding ketoesters with NaBH$_4$:

20. ethyl 5-[1-hydroxy-2-(4-(4-methyl-2-thiazolyl)-piperazino)-ethyl]-salicylate.

21. propyl 5-[1-hydroxy-2-(4-(4-methyl-2-thiazolyl)-piperazino)-ethyl]-salicylate.

22. isopropyl 5-[1-hydroxy-2-(4-(4-methyl-2-thiazolyl)-piperazino)-ethyl]-salicylate.

23. butyl 5-[1-hydroxy-2-(4-(4-methyl-2-thiazolyl)-piperazino)-ethyl]-salicylate.

24. isobutyl 5-[1-hydroxy-2-(4-(4-methyl-2-thiazolyl)-piperazino)-ethyl]-salicylate.

25. sec.-butyl 5-[1-hydroxy-2-(4-(4-methyl-2-thiazolyl)-piperazino)-ethyl]-salicylate.

EXAMPLE 26

A solution of 10 g of 2-benzyloxy-5-[1-hydroxy-2-(4-(4-methyl-2-thiazolyl)-piperazino)-ethyl]-benzamide in 200 ml of ethanol is hydrogenated on PtO$_2$ at 20° and under 1 bar until the calculated amount of hydrogen has been absorbed, and the usual working-up results in "A" m.p. 182°.

EXAMPLE 27

A solution of 10 g of 5-[4-(4-methyl-2-thiazolyl)-piperazino-acetyl]-salicylamide [obtainable from 4-(4-methyl-2-thiazolyl)-piperazine and 5-bromacetyl-salicylamide] in 200 ml of methanol is hydrogenated on 1 g of 10% Pd-charcoal at 40° and under 1 bar until the calculated amount of hydrogen has been absorbed, and filtration and evaporation result in "A"m.p. 182°.

EXAMPLE 28

A solution of 10 g of methyl 5-[1-hydroxy-2-(4-(4-methyl-2-thiazolyl)-piperazino-ethyl]-salicylate and 10 g of NH$_4$Cl in a mixture of 100 ml of saturated methanolic NH$_3$ solution and 100 ml of 25% aqueous NH$_3$ solution is left to stand at 20° for 48 hours, concentrated and subjected to the usual working-up. "A" is obtained, m.p. 182°. Dihydrochloride, m.p. 244°14 245°.

The amides indicated in Examples 2 to 9 are obtained analogously from the methyl esters indicated in Examples 12 to 19 with NH$_3$.

EXAMPLE 29

10 g of methyl 5-[1-hydroxy-2-(4-(4-methyl-2-thiazolyl)-piperazino)ethyl]-salicylate are added to a solution of 200 mg of Na in 120 ml of methanol. Methylamine is passed in for 30 min., maintaining the internal temperature below 30°. After the mixture has stood for 12 h it is concentrated, and the usual working-up results in 5-[1-hydroxy-2-(4-(4-methyl-2-thiazolyl)-piperazino)-ethyl]-N-methylsalicylamide, m.p. 252°.

EXAMPLE 30 to 37

The following are obtained in analogy to Example 29 from the corresponding methyl esters with methylamine:

30. 5-[1-hydroxy-2-(4-tetrahydrofuroyl-piperazino)ethyl]-N-methylsalicylamide.

31. 5-[1-hydroxy-2-(4-(4-methyl-2-thiazolyl)-homopiperazino)ethyl]-N-methylsalicylamide.

32. 5-[1-hydroxy-2-(4-benzamidopiperidino)ethyl]-N-methylsalicylamide.

33. 5-[1-hydroxy-2-(6,7-dimethoxy-1,2,3,4-tetrahydroisoquinolino)ethyl]-N-methylsalicylamide.

34. 5-[1-hydroxy-2-(1-imidazolyl)ethyl]-N-methylsalicylamide.

35. 5-[1-hydroxy-2-(tribromo-1-imidazolyl)ethyl]-N-methylsalicylamide.

36. 5-[1-hydroxy-2-(2-(3-indolyl)-1,1-dimethylethylamino)ethyl]-N-methylsalicylamide.

37. 5-[1-hydroxy-2-(4-(4-methyl-2-thiazolyl)-piperazinopropyl]-N-methylsalicylamide.

EXAMPLES 38 to 41

The following are obtained in analogy to Example 29 from methyl 5-[1-hydroxy-2-(4-(4-methyl-2-thiazolyl)-piperazino)-ethyl]-salicylate with the appropriate alkylamines:

38. 5-[1-hydroxy-2-(4-(4-methyl-2-thiazolyl)-piperazino)-ethyl]-N-ethylsalicylamide.

39. 5-[1-hydroxy-2-(4-(4-methyl-2-thiazolyl)-piperazino)-ethyl]-N-propylsalicylamide.

40. 5-[1-hydroxy-2-(4-(4-methyl-2-thiazolyl)-piperazino)-ethyl]-N-isopropylsalicylamide.

41. 5-[1-hydroxy-2-(4-(4-methyl-2-thiazolyl)-piperazino)-ethyl]-N-butylsalicylamide.

The examples which follow relate to pharmaceutical compositions which contain compounds of the formula I:

Example A: Tablets

A mixture of 1 kg of "A" dihydrochloride, 4 kg of lactose, 1.2 kg of maize starch, 0.2 kg of talc and 0.1 kg of magnesium stearate is compressed to tablets in a customary manner in such a way that each tablet contains 10 mg of active substance.

Example B: Coated tablets

Tablets are compressed in analogy to Example A and are then coated in a customary manner with a coating composed of sucrose, wheat starch, talc, tragacanth and colorant.

Example C: Capsules 5 kg of "A" dihydrochloride are dispensed in hard gelatin capsules in a customary manner so that each capsule contains 20 mg of the active substance.

Example D: Ampoules

A solution of 1 kg of "A" dihydrochloride in 30 liters of double-distilled water is filtered sterile, dispensed into ampoules, lyophilized under sterile conditions and sealed sterile. Each ampoule contains 5 mg of active substance.

Tablets, coated tablets, capsules or ampoules containing one or more of the other active substances of the formula I and/or the physiologically acceptable acid addition salts thereof, are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A salicylic acid derivative of the formula I

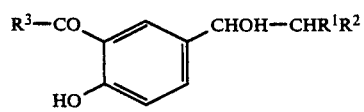

wherein
R$^1$ is H or CH$_3$,
R$^2$ is 4-(4-methyl-2-thiazolyl)-piperazino, 4-(tetrahydro-2-furoyl)-piperazino, or 4-(4-methyl-2-thiazolyl)-homopiperazino, and
R$^3$ is alkoxy having 1–4 C atoms, NH$_2$ or alkylamino having 1–4 C atoms; or a physiologically acceptable acid addition salt thereof.

2. A compound of claim 1, wherein R$^1$ is H.

3. A compound of claim 2, wherein R$^3$ is alkoxy having 1–4 C atoms.

4. A compound of claim 2, wherein R$^3$ is alkylamino having 1–4 C atoms.

5. A compound of claim 2, wherein R$^3$ is NH$_2$.

6. A compound of claim 1, which is 5-[1-hydroxy-2-(4-(4-methyl-2-thiazolyl)-piperazino)-ethyl]-salicylamide, or a physiologically acceptable acid addition salt thereof.

7. A compound of claim 1, wherein R$^2$ is 4-(4-methyl-2-thiazolyl)-piperazino.

8. A compound of claim 1, wherein R$^3$ is NH$_2$.

9. A pharmaceutical composition comprising a compound of claim 1 and a pharmaceutically acceptable excipient.

10. A method of treating cardiovascular disease, comprising administering an effective amount of a compound of claim 1.

11. A method of protecting the cardiovascular system, comprising administering an effective amount of a compound of claim 1.

12. A pharmaceutical composition comprising a compound of claim 6 and a pharmaceutically acceptable excipient.

13. A method of treating cardiovascular disease, comprising administering an effective amount of a compound of claim 6.

14. A method of protecting the cardiovascular system, comprising administering an effective amount of a compound of claim 6.

* * * * *